United States Patent
Ruijters

(10) Patent No.: US 8,488,910 B2
(45) Date of Patent: Jul. 16, 2013

(54) IMAGE PROVISION FOR REGISTRATION

(75) Inventor: Daniel Simon Anna Ruijters, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 207 days.

(21) Appl. No.: 13/130,601

(22) PCT Filed: Nov. 19, 2009

(86) PCT No.: PCT/IB2009/055171
§ 371 (c)(1),
(2), (4) Date: May 23, 2011

(87) PCT Pub. No.: WO2010/061322
PCT Pub. Date: Jun. 3, 2010

(65) Prior Publication Data
US 2011/0235890 A1    Sep. 29, 2011

(30) Foreign Application Priority Data

Nov. 25, 2008 (EP) .................................. 08169870

(51) Int. Cl.
*G06K 9/32* (2006.01)
(52) U.S. Cl.
USPC ........... 382/294; 345/419; 348/580; 128/922; 378/4
(58) Field of Classification Search
USPC ............. 382/100, 154, 128, 129, 130, 131, 382/132; 345/419–427, 648–659, 660–671; 348/578, 580, 583; 128/922; 378/4–27
See application file for complete search history.

(56) References Cited

U.S. PATENT DOCUMENTS

| | | | |
|---|---|---|---|
| 5,095,906 A | 3/1992 | Ema | |
| 6,556,695 B1* | 4/2003 | Packer et al. | 382/128 |
| 7,327,872 B2 | 2/2008 | Vaillant et al. | |
| 7,505,809 B2* | 3/2009 | Strommer et al. | 600/424 |
| 8,295,435 B2* | 10/2012 | Wang et al. | 378/65 |
| 8,332,013 B2* | 12/2012 | Strommer | 600/424 |
| 2004/0138548 A1 | 7/2004 | Strommer et al. | |

(Continued)

OTHER PUBLICATIONS

D. Ruijters et al: "Efficient GPU-Accelerated Elastic Image Registration" Proceedings of the Sixth IASTED International Conference on Biomedical Engineering, Innsbruck, Austria, Feb. 13-15, 2008, XP007912390, ACTA Press, Anaheim, CA, USA, Feb. 13, 2008, pp. 419-424.

(Continued)

*Primary Examiner* — Anand Bhatnagar

(57) ABSTRACT

The invention relates to a device and a method for providing a basis for registering a three-dimensional model of an anatomical region with two-dimensional projection images, by deriving a three-dimensional model of an anatomical region at a phase of a periodic signal; deriving two-dimensional projection images of a region which overlaps with the anatomical region re-constructed as the three-dimensional model; pre-5 selecting a subset of projection images out of the derived two-dimensional projection images, which are closest to the phase; and selecting a reference image for the registration from the subset of pre-selected projection images by choosing the projection image with the most contrast.

13 Claims, 3 Drawing Sheets

U.S. PATENT DOCUMENTS

| | | |
|---|---|---|
| 2005/0054916 A1 | 3/2005 | Mostafavi |
| 2006/0262970 A1 | 11/2006 | Boese et al. |
| 2007/0016108 A1* | 1/2007 | Camus et al. ............ 600/587 |
| 2008/0039713 A1* | 2/2008 | Thomson et al. .......... 600/411 |
| 2008/0137924 A1 | 6/2008 | Boese et al. |
| 2008/0152205 A1* | 6/2008 | Vaillant et al. ............ 382/132 |
| 2008/0221442 A1* | 9/2008 | Tolkowsky et al. ........ 600/425 |
| 2008/0287803 A1* | 11/2008 | Li et al. .................... 600/466 |
| 2010/0172567 A1* | 7/2010 | Prokoski .................. 382/132 |

OTHER PUBLICATIONS

Stuke I et al: "Cardio Dynamic Subtraction Angiography (CDSA)" Second Joint EMBS-BMES Conference 2002. Conference Proceedings. 24th. Annual International Conference of the Engineering in Medicine and Biology Society. Annual Fall Meeting of The Biomedical Engineering Society. Houston, TX, Oct. 23-26, 2002; XP010619884, vol. 2, Oct. 23, 2002, pp. 915-916.

* cited by examiner

IMAGE PROVISION FOR REGISTRATION

FIELD OF THE INVENTION

The invention relates to a device and method for providing a basis for registering a three-dimensional model of an anatomical region with two-dimensional projection images.

BACKGROUND OF THE INVENTION

In medical image registration, for example, images of a certain modality have to be transformed in the coordinate system of an image of another modality which might be taken at another point in time. Registration is necessary in order to be able to compare or integrate the images obtained from different modalities.

When a three-dimensional multi-modality dataset derived for example by magnetic resonance (MR) or computed tomography (CT), which is representing an anatomical region is going to be blended with live two dimensional x-ray projection images (e.g. for the purpose of 3D roadmapping), it is necessary that the mapping (transformation model) between the frame of registration of the x-ray system (e.g. a C-arm x-ray system) and the frame of registration of the three-dimensional multi-modality dataset is known.

The process of obtaining this mapping is called "registration". The direct registration of the three-dimensional dataset to the two-dimensional x-ray projection image can be performed either manually, or automatically, employing a registration algorithm.

With respect to the results achieved with the present registration systems there is still the desire to improve the results achieved in the registration process.

SUMMARY OF THE INVENTION

It is an object of the present invention to improve the results that can be obtained with the registration process.

This object is solved with a device and a method according to the independent claims.

Advantageous further developments are subject of the dependent claims.

According to an embodiment of the present invention, there is provided a device for providing a basis for registering a three-dimensional model of an anatomical region with two-dimensional projection images, comprising a 3D imaging system for deriving a three-dimensional model of an anatomical region at a phase of a periodic signal; a 2D imaging system for deriving two-dimensional projection images of a region which overlaps with the anatomical region reconstructed by the 3D imaging system; a pre-selector for selecting a subset of projection images out of the derived two-dimensional projection images, which are closest to the phase; and a selector for selecting a reference image for the registration from the subset of pre-selected projection images by choosing the projection image with the most contrast. With respect to the above mentioned term "periodic signal" it is noted that this is preferably the cardiac cycle. However, this can also be the respiratory cycle. In this context, a "phase" of this periodic signal refers to a specific point of time within one cycle or period of the periodic signal, and is preferably a cardiac phase, but can also be a respiratory phase. This embodiment has the advantage that the reference image is the optimal two-dimensional projection image for the registration leading to an improved outcome of the registration procedure. This facilitates minimal interventional treatment of Coronary Artery Disease (CAD), and particularly for Chronic Total Occlusions (CTO). Since the coronary arteries are the most likely anatomical structures that can drive the registration (automatic or manual), and these coronary arteries deform due to the cardiac motion, it is beneficial for the registration procedure to select an image for registration out of the x-ray sequence that closely matches the cardiac phase of the three-dimensional model and a maximum of contrast medium, in order maximally visualize the vessel tree. As a benefit thereof, the usage of contrast medium and radiation dose during the cardiac interventional procedure can be reduced.

According to a further embodiment, the device is further comprising a signal monitoring system for detecting the periodic signal; and a time allocator for assigning a time position of the periodic signal to the respective phase of the three-dimensional model. This provides the advantage that the three-dimensional model and the two-dimensional projection images can be allocated to each other by means of the cardiac cycle co-recorded with the sequence of two-dimensional projection images.

According to another embodiment, the device is further comprising a signal monitoring system for detecting the periodic signal, wherein the 2D imaging system is prospectively gated based on the periodic signal for obtaining the two-dimensional projection images within a certain time period which includes the phase of the three-dimensional model. This way, the x-rays of the 2D imaging system are turned on only at the phase (preferably the cardiac phase) for which the three-dimensional dataset was obtained. This has the advantage that x-ray radiation dose to the patient is saved. The "certain time period which includes the phase of the three-dimensional model" is preferably a time period having the phase of the three-dimensional model as a center and showing a deviation from this center of a certain percentage (assuming that one signal cycle are a 100 percent). This deviation is preferably ten percent, more preferably five percent and more preferably two percent and most preferably one percent.

According to a further embodiment, the selector is a darkness evaluator for choosing the projection image with the most contrast by choosing the darkest projection image. This provides a reliable method of finding the image with the most contrast medium present.

Alternatively, the selector is a middle locator for choosing the projection image with the most contrast by choosing the projection image which is closest to the middle with respect to a time period from the first projection image to the last projection image of the derived two-dimensional projection images. This provides the advantage, that the image with the most contrast can be selected with a minimum of hardware performance utilization.

Further, the invention provides different embodiments of a method which provide the above mentioned advantages respectively. Moreover, the invention also provides the above mentioned advantages with a device arranged to perform such a method, and an x-ray system comprising a device according to one of the above mentioned embodiments.

These and other aspects of the invention will be apparent from and elucidated with reference to the embodiments described hereafter.

It may be seen as the gist of the invention to establish or improve a registration of a three-dimensional model with a two-dimensional projection image by finding an optimal two-dimensional image as a reference image which, on one hand, corresponds to the cardiac phase of the three-dimensional model and, on the other hand, is obtained when the most contrast medium is present.

DETAILED DESCRIPTION OF EMBODIMENTS

Figure 2:
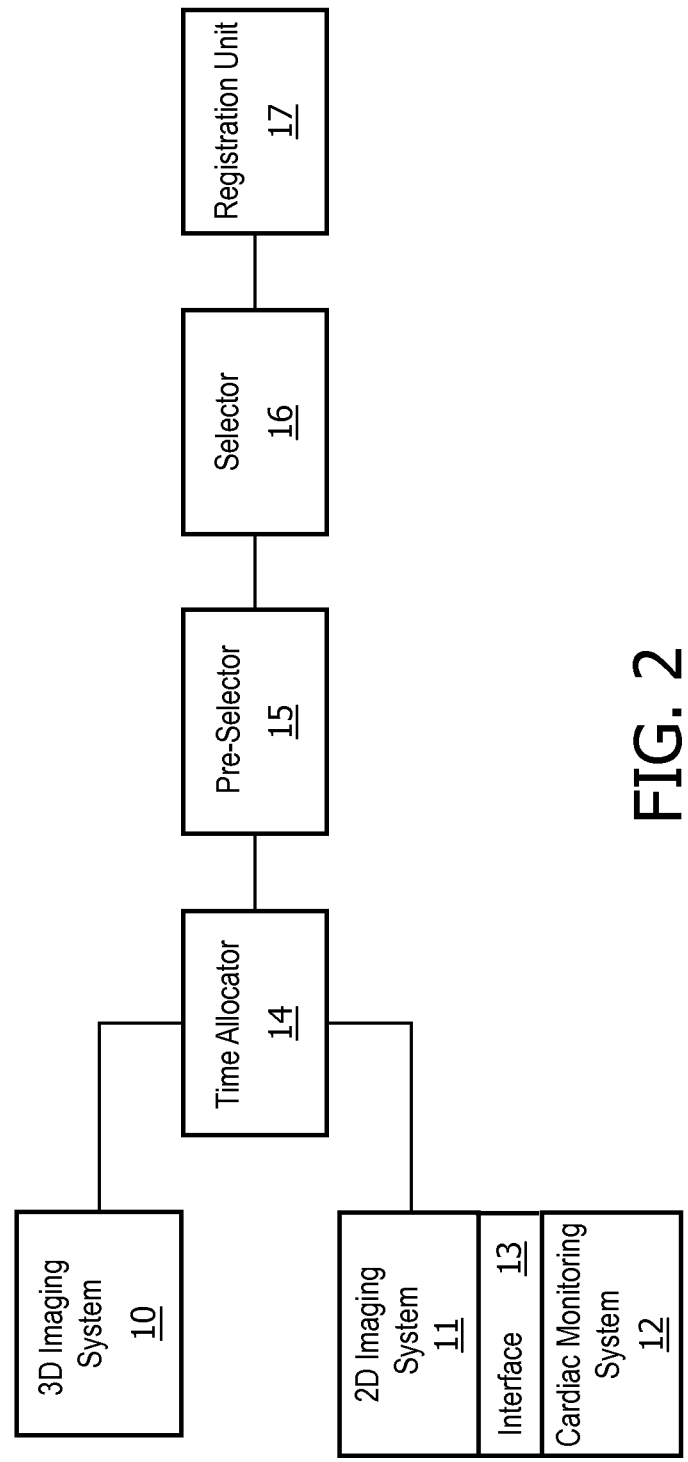
FIG. 2 shows a device according to a first, second and third embodiment of the invention.

With reference to FIG. 2, a device according to a first embodiment of the invention is described. This device comprises a 3D imaging system 10 for reconstructing an anatomical region in a three-dimensional model in the form of a static dataset. The 3D imaging system 10 can be a magnetic resonance (MR), computed tomography (CT) or ultrasound system. In this embodiment, however, computed tomography (CT) is the preferred modality. The reconstructed anatomical region is in this embodiment a heart; however, the invention is not limited thereto. Further, a 2D imaging system 11 is provided for obtaining projection images. This 2D imaging system 11 is preferably a system for achieving x-ray projection images. Moreover, reference numeral 12 depicts a cardiac monitoring system 12 for monitoring the cycle of the heart. Alternatively thereto the monitoring system 12 can also be a system for monitoring the respiratory cycle of a patient. The 2D imaging system 11 and the cardiac monitoring system 12 are both connected with each other via an interface 13 which allows correlating the outcomes of the 2D imaging system 11 and the cardiac monitoring system 12 relative to each other (according to the later described third embodiment, the interface 13 has also a control functionality). The thus achieved results are forwarded from the interface 13 to a time allocator 14, an input port of which is connected with the output of the interface 13. Another input port of the time allocator 14 is connected with the 3D imaging system 10. The time allocator 14 is adapted to allocate the x-ray projection images obtained by the 2D imaging system 11 with the cardiac phase of the three-dimensional model obtained by the 3D imaging system 10. Subsequently to the time allocator 14, a pre-selector 15 is provided for selecting a subset of projection images out of the plurality of projection images obtained by the 2D imaging system 11 which are closest to a specific cardiac phase. The output port of this pre-selector 15 is connected with the input port of a selector 16 for selecting a reference image from the plurality of pre-selected projection images forwarded by the pre-selector 15 by choosing the projection image with the most contrast. In this embodiment, the selector 16 is a darkness evaluator for choosing the darkest projection image as image with the most contrast. Subsequent to the selector 16, a registration unit 17 is provided which registers the three-dimensional dataset obtained from the 3D imaging system 10 with the reference image selected by the selector 16.

Figure 1:
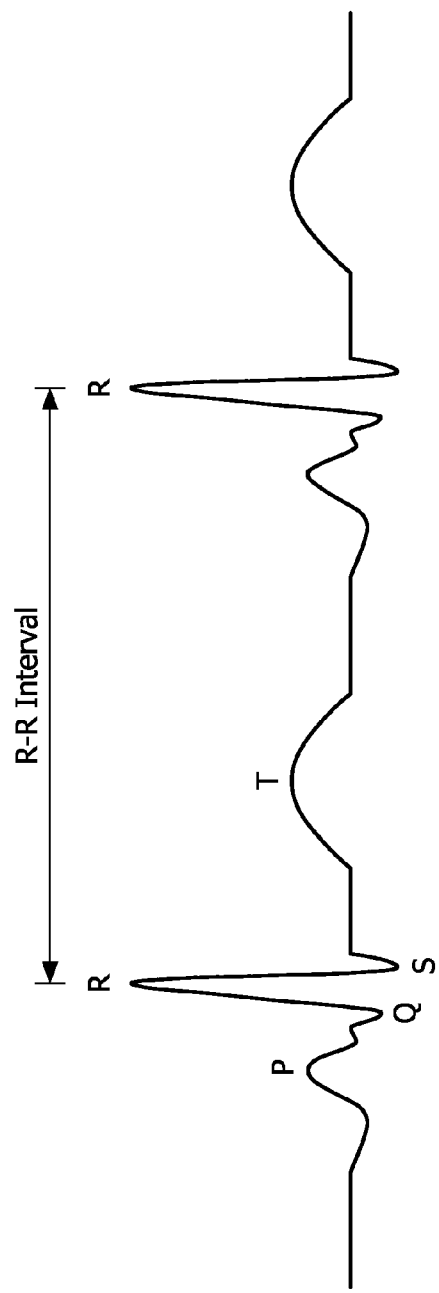
FIG. 1 schematically depicts an electrocardiogram (ECG) signal.
Figure 3:
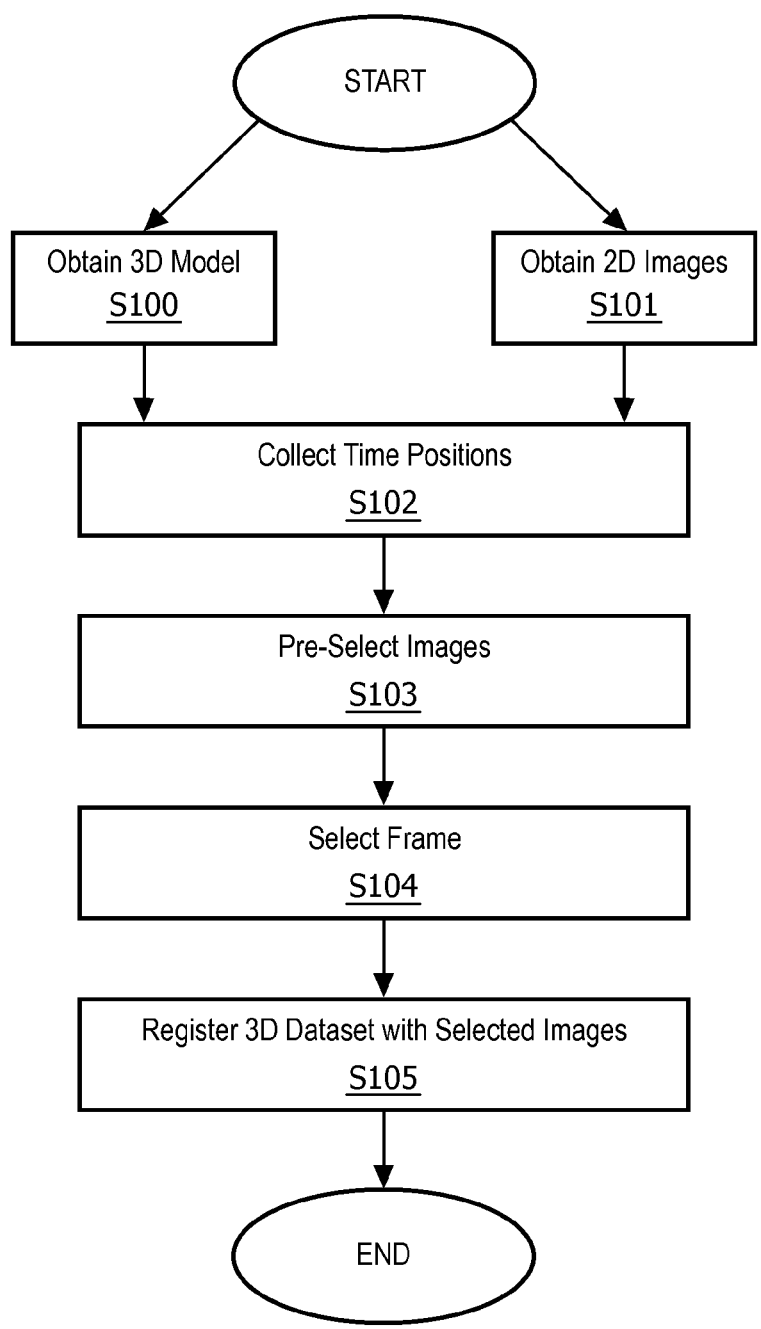
FIG. 3 is a flowchart illustrating the functionality of the device of FIG. 2.

FIG. 3 is a flowchart illustrating the functionality of the device of FIG. 2. In step S100, a cardiac three-dimensional model of the heart is obtained by the 3D imaging system 10. This model is reconstructed at a fixed cardiac phase (which is a specific point of time within the cardiac cycle). It is to be noted that the invention is not limited to using the cardiac phase, but only to a periodic signal which can also be the respiratory cycle. Since the best reconstructions of the coronary vessels of the heart are obtained when there is little cardiac motion, the diastole phase is very often used. Typically the diastole phase can be found at 75% of the R-peak interval which is depicted in FIG. 1 as the interval between two R-peaks. The obtained three-dimensional model (CT dataset) at the specific cardiac phase is preferably encoded to DICOM ("Digital Imaging and Communications in Medicine") information. In step S101, a sequence of two-dimensional x-ray projection images is obtained by the 2D imaging system 11. In order to receive better image results, a contrast medium is injected into the patient. Also in step S101, in parallel to this, a kymogram which is assigned to the x-ray image sequence by means of the interface 13 is recorded by the cardiac monitoring system 12. A kymogram is a signal that can be described as a function of time, indicating the cardiac phase. Please refer to FIG. 1, in which a kymogram is illustrated. This kymogram can be an electrocardiogram (ECG) signal that is co-recorded with the x-ray image sequence. Alternatively thereto, it is also possible that the cardiac monitoring system 12 is constructed such that it analyses the image results obtained by the 2D imaging system 11 in order to derive the cardiac cycle directly from the images. In this alternative, the cardiac monitoring system 12 extracts a kymogram directly from an analysis of the x-ray image content over the time, wherein the cardiac motion is analyzed. In this alternative, the interface 13 forwards the results of the 2D imaging system 11 to the cardiac monitoring system 12 which analyses these images in order to derive a kymogram. Then the interface 13 merges the kymogram and the image sequence and outputs them to the time allocator 14. As can be seen in FIG. 1, the R-peaks can be determined from the kymogram. The R-peaks correspond to the arterial pulse and are therefore good indicators for the beginning of a cardiac cycle. The cardiac phase is usually expressed as fraction or percentage of the interval between two consecutive R-peaks.

Having obtained the three-dimensional model of the heart based on CT in step S100 and the sequence of x-ray projection images with the corresponding kymogram in step S101, the x-ray image sequence is to be registered to the cardiac CT model as described in the following.

As described above, the three-dimensional model is reconstructed for a specific cardiac phase. Now, in step S102, the time positions which correspond to this specific cardiac phase are collected from the kymogram by the time allocator 14, wherein due to the location of the R-peaks, the beginning of each cardiac cycle is known. This delivers a set of time positions.

In step S103, from the sequence of the x-ray projection images, the frames (images) are then pre-selected that are closest to the time positions obtained in step S102. Assuming that the first frame corresponds to the time zero, the numbers of the closest frames can be derived by multiplying the individual time positions by the frame rate, and rounding to the nearest integer. The thus obtained pre-selected frames are a number of frames which are all in the correct cardiac phase which also represents the three-dimensional model.

Thereafter, in step S104, the aim is, to select the frame in which the most contrast medium is present. According to this first embodiment, in order to select the frame with the most contrast medium present, the selector 16 chooses the darkest frame from the number of pre-selected frames. The correlation that the darkest frame is also the one with the most contrast medium is based on the assumption that contrast medium absorbs x-ray radiation, and therefore the image with most contrast medium has the lowest brightness.

In the subsequent step S105, the three-dimensional dataset obtained from the 3D imaging system 10 is registered with the projection image selected by the selector 16. For this purpose, the frame selected in step S104 serves as a reference image in the registration procedure, i.e. the blending of the selected x-ray projection image with the image from the three-dimensional dataset. The conducted registration can be manual, semi-automatic or fully-automatic.

In the following, a second embodiment is described. In order to avoid repetitions, only those aspects which differentiate from the first embodiment are described.

The second embodiment differentiates from the first embodiment only in the way how the frame with the most contrast medium is selected. Thus, in the second embodiment, the selector 16 is a middle locator, which selects in step S104 the frame that is closest to the middle of the x-ray image sequence, based on the assumption that at the beginning of the sequence contrast medium is injected, flows into the vessels, and at the end of the sequence it is washed out from the heart.

In the following, a third embodiment is described. In order to avoid repetitions, only those aspects which differentiate from the first and second embodiment are described.

In this embodiment, the interface 13 has the functionality to control the 2D imaging system 11 dependent from the kymogram obtained with the cardiac monitoring system 12. Thus, this embodiment differentiates from the first and second embodiment in that the x-ray projection images in step S101 are only recorded at the cardiac phase for which the heart is reconstructed. For this purpose, the x-ray sequence is prospectively gated by the kymogram via the interface 13, i.e. the x-rays are turned on only at the cardiac phase for which the CT dataset was obtained. This has the advantage that x-ray radiation dose to the patient is saved.

In the following an example of a practical application is described. The registration of a three-dimensional coronary dataset allows overlaying of a real-time X-ray image stream on the three-dimensional coronary vasculature that was segmented from the dataset. This is very useful for guidance of intravascular devices, such as catheters. Especially for Chronic Total Occlusion (CTO) of the coronary artery, this procedure has great clinical benefit, since the occluded part of the artery, which is practically invisible in the two-dimensional x-ray image, still can be depicted in the three-dimensional dataset.

In the near future of interventional cardiology it is foreseen that diagnosis is increasingly performed on CT. Blending of the CT dataset with the cardiovascular x-ray images as described above will help to reduce the usage of contrast medium and radiation dose during the cardiac interventional procedure and may help diagnosis and interventional treatment by allowing better comparison between the CT dataset and the cardiovascular x-ray images. Also, for other areas of vascular intervention diagnostic, the CT dataset is frequently available and could be used to improve a vascular intervention.

While the invention has been illustrated and described in detail in the drawings and foregoing description, such illustration and description are to be considered illustrative or exemplary and not restrictive and it is not intended to limit the invention to the disclosed embodiments. The word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used advantageously. Any reference signs in the claims should not be construed as limiting the scope of the invention.

The invention claimed is:

1. A device for providing a basis for registering a three-dimensional model of an anatomical region with two-dimensional projection images, comprising:
    a 3D imaging system (10) for deriving a three-dimensional model of an anatomical region at a phase of a periodic signal;
    a 2D imaging system (11) for deriving two-dimensional projection images of a region which overlaps with the anatomical region reconstructed by the 3D imaging system;
    a pre-selector (15) for selecting a subset of projection images out of the derived two-dimensional projection images, which are closest to the phase; and
    a selector (16) for selecting a reference image for the registration from the subset of pre-selected projection images by choosing the projection image with the most contrast.

2. The device according to claim 1, further comprising
    a signal monitoring system (12) for detecting the periodic signal; and
    a time allocator (14) for assigning a time position of the periodic signal to the respective phase of the three-dimensional model.

3. The device according to claim 1, further comprising
    a signal monitoring system (12) for detecting the periodic signal, wherein the 2D imaging system (11) is prospectively gated based on the periodic signal for obtaining the two-dimensional projection images within a certain time period which includes the phase of the three-dimensional model.

4. The device according to claim 1, wherein the selector (16) is a darkness evaluator for choosing the projection image with the most contrast by choosing the darkest projection image.

5. The device according to claim 1, wherein the selector (16) is a middle locator for choosing the projection image with the most contrast by choosing the projection image which is closest to the middle with respect to a time period from the first projection image to the last projection image of the derived two-dimensional projection images.

6. An x-ray system comprising a device according to claim 1.

7. A method of providing a basis for registering a three-dimensional model of an anatomical region with two-dimensional projection images, comprising the steps:
    deriving a three-dimensional model (S100) of an anatomical region at a phase of a periodic signal;
    deriving two-dimensional projection images (S101) of a region which overlaps with the anatomical region reconstructed as the three-dimensional model;
    pre-selecting (S103) a subset of projection images out of the derived two-dimensional projection images, which are closest to the phase; and
    selecting (S104) a reference image for the registration from the subset of pre-selected projection images by choosing the projection image with the most contrast.

8. The method according to claim 7, further comprising the steps:
    detecting (S101) the periodic signal; and
    assigning (S102) a time position of the periodic signal to the respective phase of the three-dimensional model.

9. The method according to claim 7, further comprising the steps:
    detecting (S101) the periodic signal; and
    prospectively gating the 2D imaging system (11) based on the periodic signal for obtaining the two-dimensional projection images within a certain time period which includes the phase of the three-dimensional model.

10. The method according to claim 7, wherein in the step of selecting (S104), the darkest projection image is chosen.

11. The method according to claim 7, wherein in the step of selecting (S104), the projection image is chosen which is closest to the middle with respect to a time period from the first projection image to the last projection image of the derived two-dimensional projection images.

12. The method according to claim 7, wherein the closest frames are derived by multiplying the individual time positions by the frame rate, and rounding to the nearest integer.

13. A device arranged to perform the method according to claim 7.

* * * * *